(12) United States Patent
Korgozki et al.

(10) Patent No.: US 12,251,167 B2
(45) Date of Patent: Mar. 18, 2025

(54) GESTURE BASED SELECTION OF PORTION OF CATHETER

(71) Applicant: BIOSENSE WEBSTER (ISRAEL) LTD., Yokneam (IL)

(72) Inventors: Yan Korgozki, Zikhron Ya'akov (IL); Vadim Gliner, Haifa (IL); Ilan Goldenberg, Netanya (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 908 days.

(21) Appl. No.: 17/328,287

(22) Filed: May 24, 2021

(65) Prior Publication Data

US 2022/0370145 A1 Nov. 24, 2022

(51) Int. Cl.
*A61B 34/20* (2016.01)
*A61B 18/00* (2006.01)
*A61B 18/14* (2006.01)
*G02B 27/01* (2006.01)

(52) U.S. Cl.
CPC .......... *A61B 34/20* (2016.02); *A61B 18/1492* (2013.01); *G02B 27/017* (2013.01); *A61B 2018/00214* (2013.01); *A61B 2018/00839* (2013.01); *A61B 2018/1467* (2013.01); *A61B 2034/2057* (2016.02)

(58) Field of Classification Search
CPC .... A61B 34/20; A61B 18/1492; G02B 27/017
USPC ......................................................... 703/20
See application file for complete search history.

(56) References Cited

U.S. PATENT DOCUMENTS

| 5,078,714 | A | * | 1/1992 | Katims | A61M 25/0105 |
| | | | | | 606/38 |
| 5,341,807 | A | * | 8/1994 | Nardella | A61B 18/1492 |
| | | | | | 606/41 |
| 5,391,199 | A | * | 2/1995 | Ben-Haim | A61N 1/06 |
| | | | | | 607/122 |

(Continued)

FOREIGN PATENT DOCUMENTS

| CA | 2285342 | 10/1998 |
| EP | 0868160 | 10/1998 |

(Continued)

OTHER PUBLICATIONS

Borlich et al. (3D Mapping for PVI—Geometry, Image Integration and Incorporation of Contact Force Into Work Flow, Journal of Atrial Fibrillation, 2018, pp. 1-6) (Year: 2018).*

(Continued)

*Primary Examiner* — Iftekhar A Khan (57) ABSTRACT

In one embodiment, a medical system includes a catheter configured to be inserted into a body part of a living subject, a display configured to provide a view of at least part of a hand of a user, and a processor configured to track a position of the catheter in the body part, render to the display a three-dimensional view of an interior of an anatomical map of the body part and a representation of the catheter inside the anatomical map responsively to the tracked position, while the display is providing the view of the at least part of the hand of the user, recognize a gesture of the at least part of the hand of the user selecting a portion of the catheter, and perform an action responsively to recognizing selection by the user of the portion of the catheter.

19 Claims, 4 Drawing Sheets

(56) References Cited

U.S. PATENT DOCUMENTS

| | | | |
|---|---|---|---|
| 5,447,529 A * | 9/1995 | Marchlinski | A61N 1/40 600/374 |
| 5,469,857 A * | 11/1995 | Laurent | A61B 5/287 600/509 |
| 5,662,108 A * | 9/1997 | Budd | A61B 5/6858 600/509 |
| 5,673,704 A | 10/1997 | Marchlinski et al. | |
| 5,836,874 A * | 11/1998 | Swanson | A61B 18/1492 606/41 |
| 5,836,990 A * | 11/1998 | Li | A61N 1/056 607/28 |
| 5,891,095 A * | 4/1999 | Eggers | A61B 18/1482 604/114 |
| 5,935,079 A * | 8/1999 | Swanson | A61B 5/6858 600/509 |
| 6,239,724 B1 * | 5/2001 | Doron | G01F 1/36 340/870.07 |
| 6,304,776 B1 * | 10/2001 | Muntermann | A61B 18/1206 600/443 |
| 6,332,089 B1 * | 12/2001 | Acker | A61N 7/02 128/899 |
| 6,484,118 B1 * | 11/2002 | Govari | A61B 34/20 702/94 |
| 6,584,118 B1 * | 6/2003 | Russell | H04Q 11/0478 370/907 |
| 6,618,612 B1 * | 9/2003 | Acker | A61B 90/36 128/899 |
| 6,690,963 B2 * | 2/2004 | Ben-Haim | A61N 1/32 606/41 |
| 11,006,902 B1 * | 5/2021 | Bonyak | A61B 34/25 |
| 2002/0065455 A1 * | 5/2002 | Ben-Haim | A61B 5/0215 600/407 |
| 2003/0120150 A1 * | 6/2003 | Govari | A61B 5/0031 600/424 |
| 2004/0068178 A1 * | 4/2004 | Govari | A61B 34/20 324/207.22 |
| 2006/0100505 A1 * | 5/2006 | Viswanathan | A61B 90/36 600/424 |
| 2009/0263775 A1 * | 10/2009 | Ullrich | G09B 23/285 434/267 |
| 2013/0165854 A1 * | 6/2013 | Sandhu | G16H 20/40 604/95.01 |
| 2014/0051993 A1 * | 2/2014 | McGee | A61B 34/20 600/424 |
| 2018/0116731 A1 * | 5/2018 | State | A61B 17/07207 |
| 2018/0200018 A1 * | 7/2018 | Silva | A61B 5/066 |
| 2019/0008595 A1 * | 1/2019 | Popovic | A61B 34/20 |
| 2019/0060001 A1 * | 2/2019 | Kohli | A61B 34/20 |
| 2019/0183576 A1 * | 6/2019 | Fahim | A61B 90/36 |
| 2019/0183577 A1 * | 6/2019 | Fahim | G02B 27/01 |
| 2019/0388164 A1 * | 12/2019 | Gruionu | A61B 34/20 |
| 2020/0060765 A1 * | 2/2020 | Fahim | A61B 17/3478 |
| 2020/0321099 A1 * | 10/2020 | Holladay | G02B 27/017 |
| 2020/0357513 A1 * | 11/2020 | Katra | A61N 1/37258 |
| 2021/0169605 A1 * | 6/2021 | Calloway | A61B 34/74 |
| 2021/0338337 A1 * | 11/2021 | Calloway | G06F 3/011 |
| 2022/0096158 A1 * | 3/2022 | Flossmann | A61B 34/10 |
| 2022/0370145 A1 * | 11/2022 | Korgozki | G02B 27/017 |

FOREIGN PATENT DOCUMENTS

| | | |
|---|---|---|
| WO | WO9605768 | 2/1996 |
| WO | WO 2017/165301 | 9/2017 |

OTHER PUBLICATIONS

Liu et al. (An augmented reality system for image guidance of transcatheter procedures for structural heart disease, PLOS ONE, 2019, pp. 1-16) (Year: 2019).*

Extended European Search Report dated Oct. 19, 2022 from corresponding EP Application 22174794.2-1122.

* cited by examiner

GESTURE BASED SELECTION OF PORTION OF CATHETER

FIELD OF THE INVENTION

The present invention relates to medical devices, and in particular, but not exclusively to, catheter devices.

BACKGROUND

A wide range of medical procedures involve placing probes, such as catheters, within a patient's body. Location sensing systems have been developed for tracking such probes. Magnetic location sensing is one of the methods known in the art. In magnetic location sensing, magnetic field generators are typically placed at known locations external to the patient. A magnetic field sensor within the distal end of the probe generates electrical signals in response to these magnetic fields, which are processed to determine the coordinate locations of the distal end of the probe. These methods and systems are described in U.S. Pat. Nos. 5,391,199, 6,690,963, 6,484,118, 6,239,724, 6,618,612 and 6,332,089, in PCT International Publication No. WO 1996/005768, and in U.S. Patent Application Publications Nos. 2002/0065455 and 2003/0120150 and 2004/0068178. Locations may also be tracked using impedance or current based systems.

One medical procedure in which these types of probes or catheters have proved extremely useful is in the treatment of cardiac arrhythmias. Cardiac arrhythmias and atrial fibrillation in particular, persist as common and dangerous medical ailments, especially in the aging population.

Diagnosis and treatment of cardiac arrhythmias include mapping the electrical properties of heart tissue, especially the endocardium, and selectively ablating cardiac tissue by application of energy. Such ablation can cease or modify the propagation of unwanted electrical signals from one portion of the heart to another. The ablation process destroys the unwanted electrical pathways by formation of non-conducting lesions. Various energy delivery modalities have been disclosed for forming lesions, and include use of microwave, laser and more commonly, radiofrequency energies to create conduction blocks along the cardiac tissue wall. In a two-step procedure, mapping followed by ablation, electrical activity at points within the heart is typically sensed and measured by advancing a catheter containing one or more electrical sensors into the heart, and acquiring data at a multiplicity of points. These data are then utilized to select the endocardial target areas at which the ablation is to be performed.

Electrode catheters have been in common use in medical practice for many years. They are used to stimulate and map electrical activity in the heart and to ablate sites of aberrant electrical activity. In use, the electrode catheter is inserted into a major vein or artery, e.g., femoral vein, and then guided into the chamber of the heart of concern. A typical ablation procedure involves the insertion of a catheter having a one or more electrodes at its distal end into a heart chamber. A reference electrode may be provided, generally taped to the skin of the patient or by means of a second catheter that is positioned in or near the heart. RF (radio frequency) current is applied through the tip electrode(s) of the ablating catheter, and current flows through the media that surrounds it, i.e., blood and tissue, between the tip electrode(s) and an indifferent electrode. The distribution of current depends on the amount of electrode surface in contact with the tissue as compared to blood, which has a higher conductivity than the tissue. Heating of the tissue occurs due to its electrical resistance. The tissue is heated sufficiently to cause cellular destruction in the cardiac tissue resulting in formation of a lesion within the cardiac tissue which is electrically non-conductive.

Therefore, when placing an ablation or other catheter within the body, particularly near the endocardial tissue, it is desirable to have the distal tip of the catheter in direct contact with the tissue. The contact can be verified, for example, by measuring the contact between the distal tip and the body tissue. U.S. Patent Application Publication Nos. 2007/0100332, 2009/0093806 and 2009/0138007, describe methods of sensing contact pressure between the distal tip of a catheter and tissue in a body cavity using a force sensor embedded in the catheter.

A number of references have reported methods to determine electrode-tissue contact, including U.S. Pat. Nos. 5,935,079; 5,891,095; 5,836,990; 5,836,874; 5,673,704; 5,662,108; 5,469,857; 5,447,529; 5,341,807; 5,078,714; and Canadian Patent Application 2,285,342. A number of these references, e.g., U.S. Pat. Nos. 5,935,079, 5,836,990, and 5,447,529 determine electrode-tissue contact by measuring the impedance between the tip electrode and a return electrode. As disclosed in the '529 patent, it is generally known than impedance through blood is generally lower that impedance through tissue. Accordingly, tissue contact has been detected by comparing the impedance values across a set of electrodes to premeasured impedance values when an electrode is known to be in contact with tissue and when it is known to be in contact only with blood.

SUMMARY

There is provided in accordance with still another embodiment of the present disclosure, a medical system including a catheter configured to be inserted into a body part of a living subject, a display configured to provide a view of at least part of a hand of a user, and a processor configured to track a position of the catheter in the body part, render to the display a three-dimensional view of an interior of an anatomical map of the body part and a representation of the catheter inside the anatomical map responsively to the tracked position, while the display is providing the view of the at least part of the hand of the user, recognize a gesture of the at least part of the hand of the user selecting a portion of the catheter, and perform an action responsively to recognizing selection by the user of the portion of the catheter.

Further in accordance with an embodiment of the present disclosure, the system includes a camera configured to capture an image of the at least part of the hand of the user, wherein the processor is configured to recognize the gesture of the at least part of the hand of the user selecting the portion of the catheter responsively to the tracked position of the catheter and the captured image.

Still further in accordance with an embodiment of the present disclosure, the system includes a head-mounted apparatus configured to be worn by the user, and including the display, which is configured to concurrently render to the display the three-dimensional view of the interior of the anatomical map of the body part, the representation of the catheter inside the anatomical map responsively to the tracked position, and the image of the at least part of the hand of the user captured by the camera.

Additionally in accordance with an embodiment of the present disclosure, the system includes a head-mounted apparatus configured to be worn by the user, and including the display, which includes an optical see-through display configured to provide the view of the at least part of the hand of the user visible through the display while augmenting the display with virtual objects including the three-dimensional view of the interior of the anatomical map of the body part, and the representation of the catheter inside the anatomical map responsively to the tracked position.

Moreover, in accordance with an embodiment of the present disclosure the catheter includes a plurality of electrodes, the processor is configured to track a position of the electrodes, and the processor is configured to recognize the gesture of the at least part of the hand of the user selecting one electrode of the electrodes of the catheter.

Further in accordance with an embodiment of the present disclosure the one electrode is configured to sense electrical activity from tissue of the body part, and the processor is configured to render to the display an intracardiac electrogram responsively to the sensed electrical activity and recognizing the gesture selecting the one electrode.

Still further in accordance with an embodiment of the present disclosure the one of the electrodes is configured to sense electrical activity from tissue of the body part, and the processor is configured to generate an electro-anatomical map responsively to the sensed electrical activity and recognizing the gesture selecting the one electrode.

Additionally, in accordance with an embodiment of the present disclosure the gesture includes any one or more of the following a pinching gesture, a pointing gesture, or a touching gesture.

Moreover in accordance with an embodiment of the present disclosure, the system includes a head-mounted apparatus configured to be worn by the user, and including the display, and wherein the processor is configured to receive user input maneuvering a virtual camera responsively to movement of the head-mounted apparatus, and render to the display the three-dimensional view of the interior of the anatomical map of the body part and the representation of the catheter inside the anatomical map as viewed from the virtual camera, while the display is providing the view of the at least part of the hand of the user.

Further in accordance with an embodiment of the present disclosure the catheter includes an expandable distal end assembly, and a plurality of electrodes disposed on the expandable distal end assembly, and the processor is configured to render to the display the three-dimensional view of the interior of the anatomical map of the body part and the representation of the catheter inside the anatomical map as viewed from a virtual camera disposed inside the expandable distal end assembly, while the display is providing the view of the at least part of the hand of the user.

There is also provided in accordance with another embodiment of the present disclosure, a medical method including providing a view of at least part of a hand of a user on a display, tracking a position of a catheter in a body part of a living subject, rendering to the display a three-dimensional view of an interior of an anatomical map of the body part and a representation of the catheter inside the anatomical map responsively to the tracked position, while the display is providing the view of the at least part of the hand of the user, recognizing a gesture of the at least part of the hand of the user selecting a portion of the catheter, and performing an action responsively to recognizing selection by the user of the portion of the catheter.

Still further in accordance with an embodiment of the present disclosure, the method includes capturing an image of the at least part of the hand of the user, wherein the recognizing includes recognizing the gesture of the at least part of the hand of the user selecting the portion of the catheter responsively to the tracked position of the catheter and the captured image.

Additionally, in accordance with an embodiment of the present disclosure the display is included in a head-mounted apparatus to be worn by the user, and the rendering includes rendering to the display the three-dimensional view of the interior of the anatomical map of the body part, the representation of the catheter inside the anatomical map responsively to the tracked position, and the captured image of the at least part of the hand of the user.

Moreover, in accordance with an embodiment of the present disclosure the providing includes providing the view of the at least part of the hand of the user visible through an optical see-through display included in a head-mounted apparatus to be worn by the user, while augmenting the display with virtual objects including the three-dimensional view of the interior of the anatomical map of the body part, and the representation of the catheter inside the anatomical map responsively to the tracked position.

Further in accordance with an embodiment of the present disclosure, the method includes tracking a position of electrodes of the catheter, and wherein the recognizing includes recognizing the gesture of the at least part of the hand of the user selecting one electrode of the electrodes of the catheter.

Still further in accordance with an embodiment of the present disclosure, the method includes sensing electrical activity from tissue of the body part by the one electrode, and wherein the rendering includes rendering to the display an intracardiac electrogram responsively to the sensed electrical activity and the recognizing the gesture selecting the one electrode.

Additionally, in accordance with an embodiment of the present disclosure, the method includes sensing electrical activity from tissue of the body part by the one electrode, and generating an electro-anatomical map responsively to the sensed electrical activity and the recognizing the gesture selecting the one electrode.

Moreover, in accordance with an embodiment of the present disclosure the gesture includes any one or more of the following a pinching gesture, a pointing gesture, or a touching gesture.

Further in accordance with an embodiment of the present disclosure, the method includes receiving user input maneuvering a virtual camera responsively to movement of a head-mounted apparatus worn by the user, and wherein the rendering includes rendering to the display the three-dimensional view of the interior of the anatomical map of the body part and the representation of the catheter inside the anatomical map as viewed from the virtual camera, while the display is providing the view of the at least part of the hand of the user.

Still further in accordance with an embodiment of the present disclosure the rendering includes rendering to the display the three-dimensional view of the interior of the anatomical map of the body part and the representation of the catheter inside the anatomical map as viewed from a virtual camera disposed inside an expandable distal end assembly of the catheter, while the display is providing the view of the at least part of the hand of the user.

There is also provided in accordance with still another embodiment of the present disclosure, a software product, including a non-transient computer-readable medium in which program instructions are stored, which instructions, when read by a central processing unit (CPU), cause the CPU to track a position of a catheter in a body part of a living subject, render to a display a three-dimensional view of an interior of an anatomical map of the body part, and a representation of the catheter inside the anatomical map responsively to the tracked position, while the display is providing a view of at least part of a hand of a user, recognize a gesture of the at least part of the hand of the user selecting a portion of the catheter, and perform an action responsively to recognizing selection by the user of the portion of the catheter.

BRIEF DESCRIPTION OF THE DRAWINGS

The present invention will be understood from the following detailed description, taken in conjunction with the drawings in which.

DESCRIPTION OF EXAMPLE EMBODIMENTS

Overview

As mentioned previously, in a two-step procedure, mapping followed by ablation, electrical activity at points within the heart is typically sensed and measured by advancing a catheter containing one or more electrodes into the heart, and acquiring data at a multiplicity of points. These data are then utilized to select the target areas at which the ablation is to be performed.

In particular, the electrical activity may be displayed as intracardial electrogram (IEGM) traces for analysis by a physician in order to find sources of arrhythmia. A catheter electrode, which is not in contact with tissue in the heart, generally measures some electrical signal from the heart tissue and a far field signal. When the catheter electrode is in contact with the heart tissue, the amplitude of the signal is mainly based on tissue conductivity, while the far field is minor. Therefore, the physician is generally interested in analyzing the IEGM traces of electrodes in contact with the tissue.

For focal catheters with one or two electrodes, a single IEGM trace is typically displayed for a physician to analyze. A physician can quickly determine based on the form of the signal whether the catheter electrode providing the signal is in contact with the tissue. However, multi-electrode catheters simultaneously capturing electrical activity from different tissue locations may provide data for a plurality of IEGM traces to be displayed at the same time on a single display. In some cases, the number of IEGM traces may be too numerous for the physician to easily determine which of the IEGM traces are provided by electrodes in contact with the tissue, and which are not.

An example of a multielectrode catheter is the Octaray® catheter, with in excess of 48 electrodes, produced by Biosense Webster Inc., of Irvine, CA, USA. The Octaray includes eight deflectable arms disposed at the distal end of a shaft, with each of the deflectable arms including six electrodes. Some catheters such as basket catheters may include more electrodes, for example, but not limited to, 120 electrodes.

In addition of the need to determine electrode contact during mapping discussed above, the physician performing an ablation procedure monitors the contact of electrodes with tissue, as effective ablation generally requires sufficient contact between the ablation electrode(s) and the tissue. For small numbers of electrodes, monitoring the contact may be performed by presenting a measure of the contact, such as the impedance seen by an electrode or the force on the electrode, numerically or even graphically. However, as the number of active electrodes used in an ablation procedure increases, it becomes increasingly difficult for the physician to monitor any parameter for the individual electrodes. In the case of electrode contact, this problem is exacerbated by the fact that in most cases as the contact varies, so the parameter measuring the contact also varies.

Embodiments of the present invention solve the above problems during a medical procedure such as a mapping or ablation procedure, by providing a user interface in which the user views a three-dimension (3D) representation of a catheter and its electrodes inside an anatomical map of a body part such as a cardiac chamber. The anatomical map may include anatomical features and/or tags identifying previous ablation points or information such as electrical activation information. The user can then easily see the catheter with respect to the body part (and its features), for example, which electrodes are in sufficient contact with tissue of the body part. A hand or hands (or part thereof) of the user may also be shown on the screen (for example, by using a see-through display of a head-mounted display (HMD), or via capturing images of the hand(s) with a camera mounted in the room or on an HMD, described in more detail below) along with the catheter representation and anatomical map so that the user can make hand gestures (which are recognized by software) to select portions of the catheter, such as one or more of the electrodes. An action associated with the selection may then be performed, for example, displaying an IEGM sensed by the selected electrode, or capturing electrical activity from the selected electrode into an electro-anatomical map. Different gesture types may be used to perform different actions. For example, the user may point to an electrode to view the IEGM associated with that electrode or pinch an electrode to select the electrode for mapping purposes.

In some embodiments, the user wears an HMD including an eye-level video display screen and a forward-facing camera. The camera captures images of the user's hand(s) (or part thereof) and displays the images of the hand(s) (or part thereof) along with the 3D catheter representation and interior 3D view of the anatomical map on the eye-level video display screen. The image of the hands and/or the catheter representation are scaled accordingly so that a finger or fingers of the user may easily select a single electrode, while the finger(s) can move around easily to select any electrode on the catheter. In some embodiments, the catheter representation and the interior of the anatomical map may be viewed from the point of view of a virtual camera which may be maneuvered by the user moving the (HMD) for example, in a different orientation and/or location. In some embodiments, the virtual camera may be disposed inside an expandable distal end assembly (e.g., basket) of the catheter.

In some embodiments, the HMD includes an optical see-through display which provides a view of the hand(s) (or part thereof) as seen through the display, while augmenting the display with virtual objects including the 3D representation of the catheter and the 3D view of the interior of the anatomical map of the body part responsively to a tracked position of the catheter.

In some embodiments, the view of the hands, representation of the catheter, and the interior of the anatomical map may be displayed on a display monitor, tablet or any suitable display device.

System Description

Figure 1:
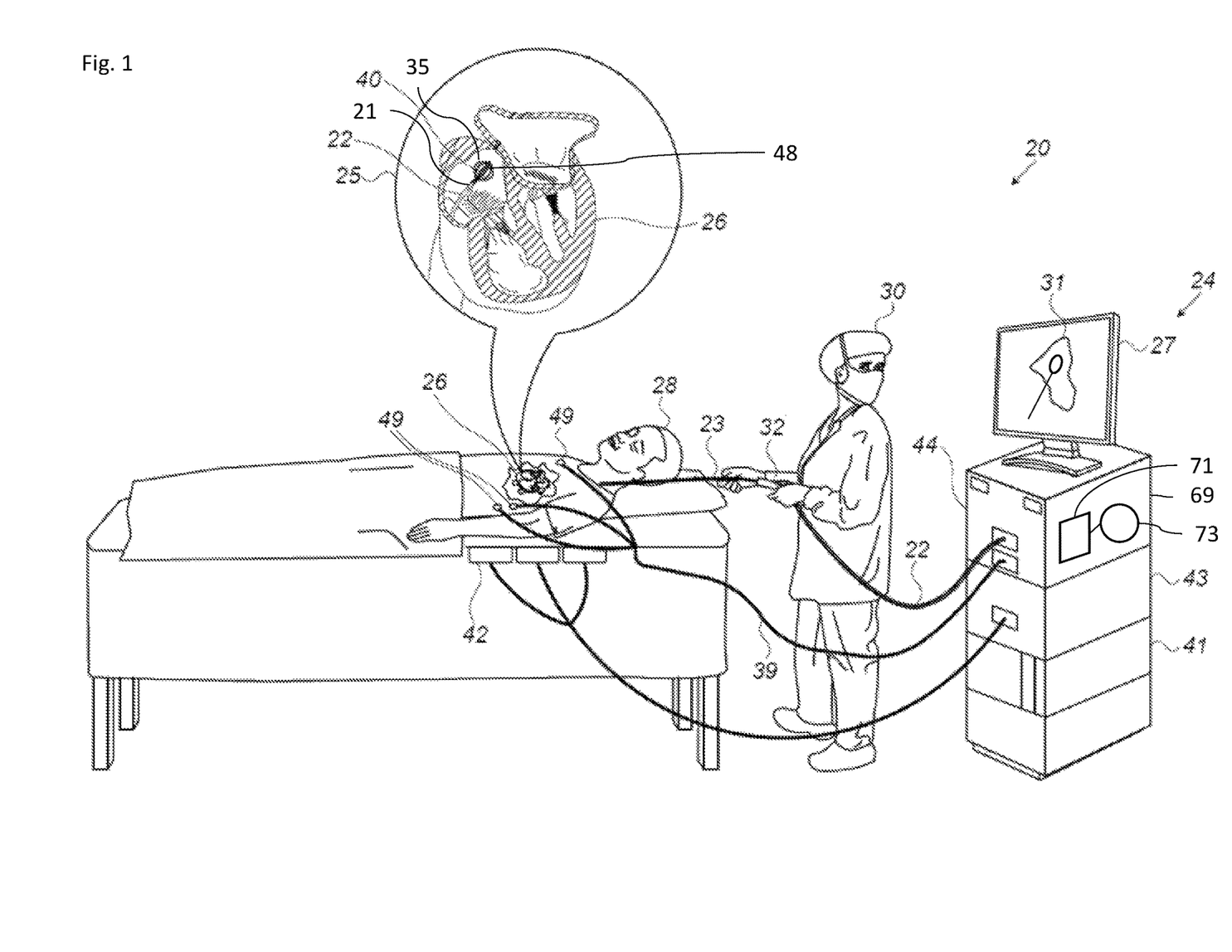
FIG. 1 is a schematic view of a medical system constructed and operative in accordance with an embodiment of the present invention.

Reference is now made to FIG. 1, which is a schematic view of a medical system 20 constructed and operative in accordance with an embodiment of the present invention. The system 20 includes a catheter 40 configured to be inserted into a body part of a living subject (e.g., a patient 28). A physician 30 navigates the catheter 40 (for example, a basket catheter produced Biosense Webster, Inc. of Irvine, CA, USA), to a target location in a heart 26 of the patient 28, by manipulating an elongated deflectable element 22 of the catheter 40, using a manipulator 32 near a proximal end of the catheter 40, and/or deflection from a sheath 23. In the pictured embodiment, physician 30 uses catheter 40 to perform electro-anatomical mapping of a cardiac chamber and ablation of cardiac tissue.

Catheter 40 includes an expandable distal end assembly 35 (e.g., a basket assembly), which is inserted in a folded configuration, through sheath 23, and only after the catheter 40 exits sheath 23 does the distal end assembly 35 regain its intended functional shape. By containing distal end assembly 35 in a folded configuration, sheath 23 also serves to minimize vascular trauma on its way to the target location.

Catheter 40 includes a plurality of electrodes 48 disposed on the expandable distal end assembly 35 for sensing electrical activity and/or applying ablation power to ablate tissue of the body part. The catheter 40 may also include a proximal electrode 21 disposed on the deflectable element 22 proximal to the expandable distal end assembly 35. Catheter 40 may incorporate a magnetic position sensor (not shown) at the distal edge of deflectable element 22 (i.e., at the proximal edge of the distal end assembly 35). Typically, although not necessarily, the magnetic sensor is a Single-Axis Sensor (SAS). A second magnetic sensor (not shown) may be included at any suitable position on the assembly 35. The second magnetic sensor may be a Triple-Axis Sensor (TAS) or a Dual-Axis Sensor (DAS), or a SAS by way of example only, based for example on sizing considerations. The magnetic sensors, the proximal electrode 21, and electrodes 48 disposed on the assembly 35 are connected by wires running through deflectable element 22 to various driver circuitries in a console 24.

In some embodiments, system 20 comprises a magnetic-sensing sub-system to estimate an ellipticity of the basket assembly 35 of catheter 40, as well as its elongation/retraction state, inside a cardiac chamber of heart 26 by estimating the elongation of the basket assembly 35 from the distance between the magnetic sensors. Patient 28 is placed in a magnetic field generated by a pad containing one or more magnetic field generator coils 42, which are driven by a unit 43. The magnetic fields generated by coil(s) 42 transmit alternating magnetic fields into a region where the body-part is located. The transmitted alternating magnetic fields generate signals in the magnetic sensors, which are indicative of position and/or direction. The generated signals are transmitted to console 24 and become corresponding electrical inputs to a processor 41.

The method of position and/or direction sensing using external magnetic fields and magnetic sensors, is implemented in various medical applications, for example, in the CARTO® system, produced by Biosense-Webster, and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1.

Processor 41, typically part of a general-purpose computer, is further connected via a suitable front end and interface circuits 44, to receive signals from body surface-electrodes 49. Processor 41 is connected to body surface-electrodes 49 by wires running through a cable 39 to the chest of patient 28.

In an embodiment, processor 41 renders to a display 27, a representation 31 of at least a part of the catheter 40 and a mapped body-part (e.g., anatomical or electro-anatomical map), responsively to computed position coordinates of the catheter 40.

Processor 41 is typically programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

The medical system 20 may also include an ablation power generator 69 (such as an RF signal generator) configured to be connected to the catheter 40, and apply an electrical signal between one or more of the electrodes 48 and the proximal electrode 21. The medical system 20 may also include an irrigation reservoir 71 configured to store irrigation fluid, and a pump 73 configured to be connected to the irrigation reservoir 71 and the catheter 40, and to pump the irrigation fluid from the irrigation reservoir 71 via an irrigation tube through irrigation holes of the catheter 40.

The example illustration shown in FIG. 1 is chosen purely for the sake of conceptual clarity. FIG. 1 shows only elements related to the disclosed techniques for the sake of simplicity and clarity. System 20 typically comprises additional modules and elements that are not directly related to the disclosed techniques, and thus are intentionally omitted from FIG. 1 and from the corresponding description. The elements of system 20 and the methods described herein may be further applied, for example, to control an ablation of tissue of heart 26.

The catheter 40 has been described herein as a basket catheter. The expandable distal end assembly 35 may include any suitable number of splines, any suitable number of electrodes, and any suitable number of electrodes per spline. The catheter 40 may be implemented as any suitable catheter-type, for example, a balloon catheter, a lasso-shape catheter, a grid-shape catheter, or a flexible spline catheter where distal ends of flexible splines are not connected together.

Figure 2:
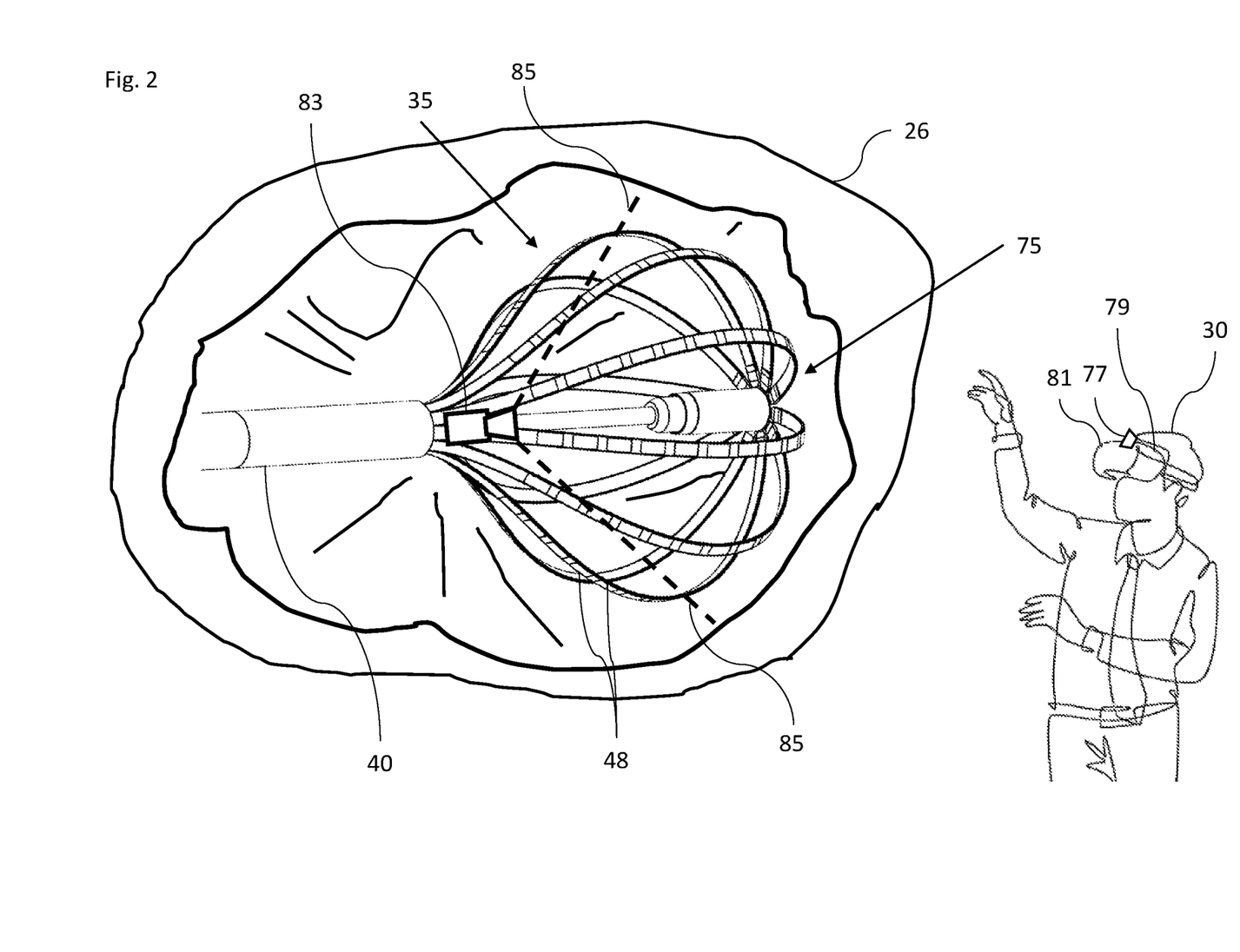
FIG. 2 is a schematic view showing a catheter inside a body part for use in the system of FIG. 1.

Reference is now made to FIG. 2, which is a schematic view showing the catheter 40 inside a body part such as the heart 26 for use in the system 20 of FIG. 1. FIG. 2 shows that some of the electrodes 48 (the ones visible in FIG. 2—only some labeled for the sake of simplicity) on the expandable distal end assembly 35 are not in contact with tissue of the heart 26, whereas other electrodes 48 (not visible in FIG. 2 but indicated using an arrow 75) are in contact with the tissue of the heart 26. The position (location and orientation) of the catheter 40 and the electrodes 48 may be tracked using any suitable tracking method, for example, the method described above with reference to FIG. 1.

The physician 30 or another user of the medical system 20 may use a display such as the display 27 (FIG. 1), or a head-mounted apparatus 79 (e.g., head-mounted display (HMD)) including a display screen 81, to view the position of the catheter 40 and the electrodes 48 with respect to the body part. The catheter 40, the electrodes 48, and the interior of the body part may be viewed from a virtual camera 83, which may be virtually placed in the body part and/or in the expandable distal end assembly 35 (as shown in FIG. 2) and maneuvered by the physician 30. The virtual camera 83 may be maneuvered using a user interface (such as a joystick) and/or by moving the head-mounted apparatus 79. FIG. 2 shows dotted lines 85, which indicate the field of view of the virtual camera 83.

The physician 30 may select portions of the catheter 40 including one or more of the electrodes 48 using hand gestures. The hand(s) (or part thereof) of the physician 30 (or images of the hand(s)) may also be shown on the display 81 (or other suitable display) so that the physician 30 can view his/her hand(s) with respect to a representation of the catheter 40 and electrodes 48 on the display 81, as described in more detail below with reference to FIG. 3.

The hand gestures may be tracked by analyzing images captured with a camera 77. The camera 77 may be disposed in the room where the medical procedure is being performed, or on the front of the head-mounted apparatus 79 or any suitable location. Alternatively, or additionally, the hand gestures may be tracked using any suitable tracking technique, for example, a glove-based technology using virtual-reality gloves with sensors in the gloves to track hand and finger movement of the physician 30 who is wearing the gloves. The sensors may include any one or more of the following sensors: mechanical; piezoresistive; or fiber-optic to measure bending of fingers. Other sensors include: a gyroscope, accelerometer(s), and/or magnetometer(s) to track movement of the hands. The signals from the gloves are sent to the processor 41 to be processed by software to identify hand movements and/or gestures.

The head-mounted apparatus 79 is configured to be worn by the physician 30 (or any suitable user). It should be noted that when the physician 30 is described herein as performing a task, the task may also be performed by any suitable user. In some embodiments, the display 81 comprises an optical see-through display in which the physician 30 can see his/her hands (or part thereof) through the display 81 when his/her hands are placed out in front of him/her. In other embodiments, the display 81 is an eye-level video display, in which images (e.g., a video) of the hand(s) (or part thereof) captured by the camera 77 are shown on the display 81, as described in more detail with reference to FIG. 3.

Figure 3:
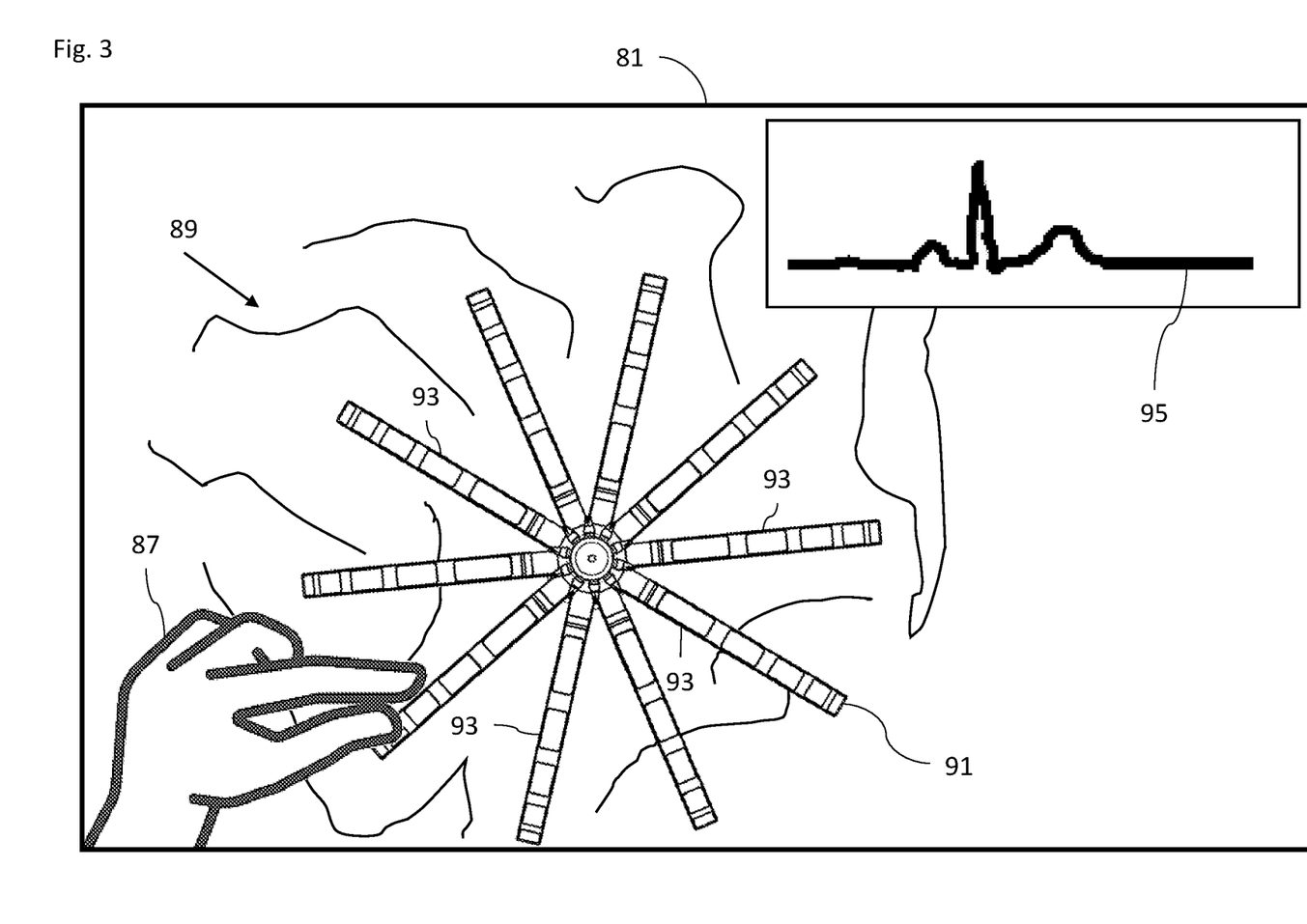
FIG. 3 is a schematic view of a display providing a view of a hand performing a gesture, and a rendering an interior of an anatomical map of a body part and a representation of the catheter of FIG. 2 inside the anatomical map.

Reference is now made to FIG. 3, which is a schematic view of the display 81 providing a view 87 of a hand performing a gesture, and a rendering of an interior of an anatomical map 89 of a body part and a rendering of a representation 91 of the catheter 40 of FIG. 2 inside the anatomical map 89. Reference is also made to FIG. 2.

FIG. 3 shows the inside of the expandable distal end assembly 35 with the electrodes 48 of the expandable distal end assembly 35 hidden from view as electrodes 48 are facing the tissue of the body part (i.e., into the page of the drawing of FIG. 3). In order to allow the physician 30 to view and select the "hidden" electrodes 48, the positions of the electrodes 48 are shown on the representation 91 as representations 93 (only some labeled for the sake of simplicity). FIG. 3 shows the hand (view 87) performing a pinching action on one of the representations 93. The corresponding electrode 48 is then selected. In the example of FIG. 3, the pinching action causes the display of an IEGM 95 sensed by the selected electrode 48. In some embodiments, the representation 91 may show the catheter 40 using a semi-transparent rendering in order to see the positions of the "hidden" electrodes 48.

In embodiments where the display 81 of the head-mounted apparatus 79 comprises an optical see-through display, the view 87 seen on the display 81 is the actual hand(s) of the physician 30 placed in front of him/her. The anatomical map 89 and the representation 91 (including the representations 93) are then augmented onto the display 81 so that the hand(s) is seen with the anatomical map 89 and the representation 91 of the catheter 40. The movement of the hands may be registered with the coordinate frame used to track the catheter 40 based on images captured by the camera 77 or using tracking gloves worn by the physician 30 or any suitable method. The size of the representation 91 and the anatomical map 89 is scaled according to the size of the hands viewed on the display 81 (either based on actual captured images of the hands or based on an assumed size of the hands) so that a gesture such as pointing with a finger or pinching with two fingers may be used to easily select a single electrode.

In embodiments where the display 81 of the head mounted apparatus 79 is an eye-level video display, the view 87 includes images (e.g., a video) of the hand(s) (or part thereof) captured by the camera 77. The view 87, anatomical map 89, and the representation 91 (including the representations 93) are rendered to the display 81 by the processor 41. The movement of the hands may be registered with the coordinate frame used to track the catheter 40 based on images captured by the camera 77 or using tracking gloves worn by the physician 30 or any suitable method. The size of the view 87 of the hands, and/or the representation 91 and the anatomical map 89, may be scaled so that a gesture such as pointing with a finger or pinching with two fingers may be used to easily select a single electrode.

Figure 4:
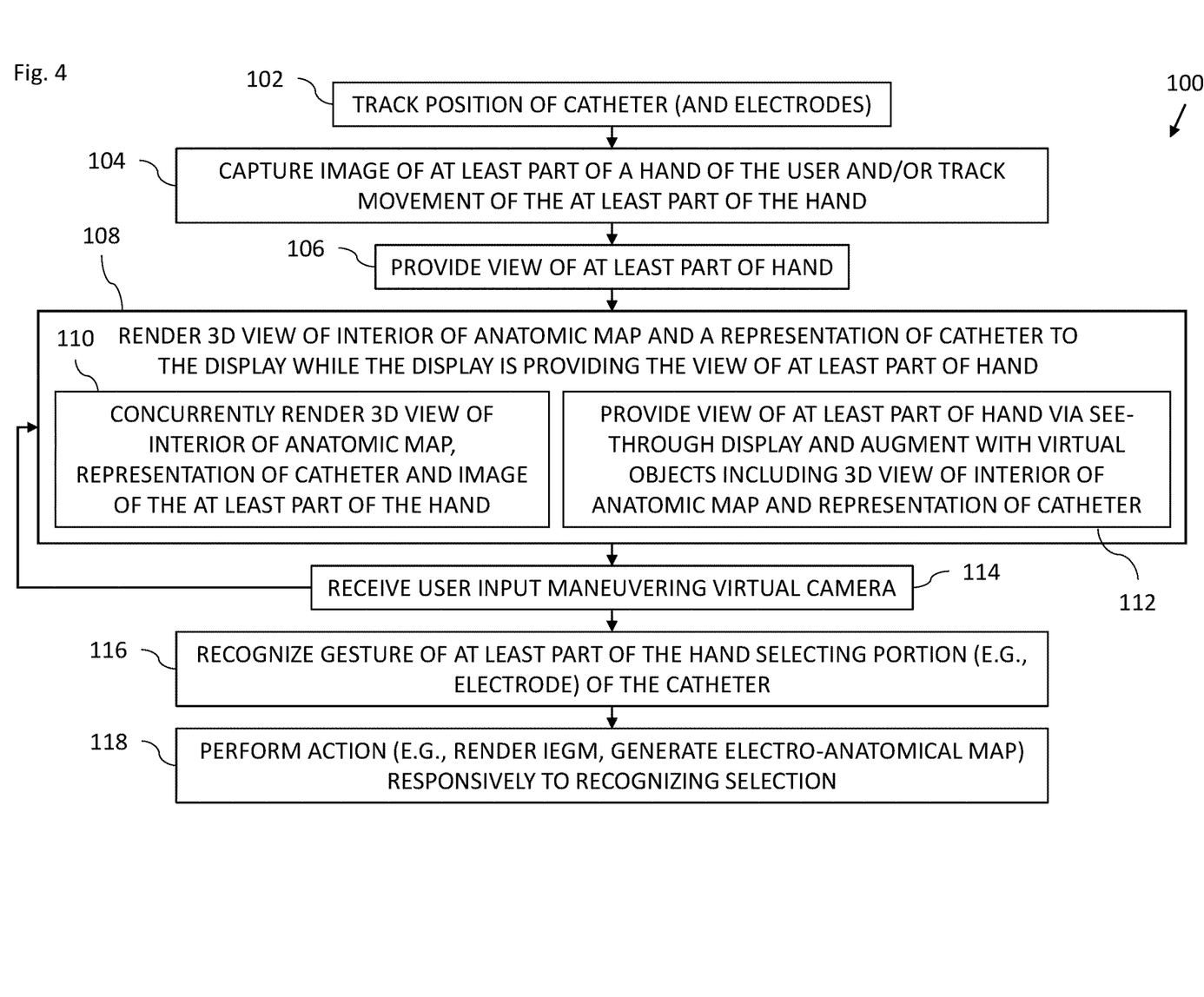
FIG. 4 is a flowchart including steps in a method of operation of the system of FIG. 1.

Reference is now made to FIG. 4, which is a flowchart 100 including steps in a method of operation of the system 20 of FIG. 1. Reference is also made to FIG. 2. The steps described below with reference to the flowchart 100 may be performed in any suitable order and some of the steps may be performed concurrently, unless the steps require a given processing order.

The catheter 40 is configured to be inserted into a body part (e.g., a chamber of the heart 26) of a living subject. The electrodes 48 of the catheter 40 and the electrodes 48 of the catheter 40 are configured to sense electrical activity from tissue of the body part. The processor 41 (FIG. 1) is configured to track (block 102) a position (e.g., location, orientation, and roll) of the catheter 40 in the body part. In some embodiments, the processor is configured to track a position of the electrodes 48 of the catheter 40. Any suitable tracking method may be used, for example, the tracking method described above with reference to FIG. 1.

In embodiments including the camera 77, the camera 77 is configured to capture (block 104) at least one image (e.g., a video) of the hand(s) (or part thereof) of the physician 30.

The display 81 is configured to provide (block 106) the view 87 (FIG. 3) of the hand(s) (or part thereof) of the physician 30. In embodiments where the display 81 of the head-mounted apparatus 79 comprises an optical see-through display, the view 87 seen on the display 81 is the actual hand(s) of the physician 30 placed in front of him/her. In embodiments where the display 81 of the head mounted apparatus 79 is an eye-level video display, the view 87 includes images (e.g., a video) of the hand(s) (or part thereof) captured by the camera 77 and the processor 41 is configured to render the images of the hand(s) (or part thereof) to the display 81.

The processor 41 is configured to render (block 108) to the display 81 the three-dimensional view of the interior of the anatomical map 89 of the body part and the representation 91 of the catheter 40 (and the representations 93 of the electrodes 48) inside the anatomical map 89 responsively to the tracked position of the catheter 40, while the display 81 is providing the view 87 of the hand(s) (or part thereof) of the physician 30. In some embodiments, the processor 41 is configured to render to the display 81 the three-dimensional view of the interior of the anatomical map 89 of the body part and the representation 91 of the catheter 40 (and the representations 93 of the electrodes 48) inside the anatomical map 89 as viewed from the virtual camera 83, while the display 81 is providing the view of the hand(s) (or part thereof) of the physician 30. The virtual camera 83 is optionally disposed inside the expandable distal end assembly 35 of the catheter 40.

In some embodiments, where the display 81 is a video display comprised in the head mounted apparatus 79, the display 81 is configured to concurrently render (block 110) to the display 81: the three-dimensional view of the interior of the anatomical map 89 of the body part; the representation 91 of the catheter 40 (and the representations 93 of the electrodes 48) inside the anatomical map 89 responsively to the tracked position of the catheter 40; and the view 87 of the hand(s) (or a part thereof) of the physician 30 included in the images (e.g., video) captured by the camera 77. In some embodiments, the processor 41 may be configured to generate the view 87 based on virtual-reality gloves worn by the physician 30.

In some embodiments, where the display 81 is comprised in the head-mounted apparatus 79, and includes an optical see-through display, the optical see-through display is configured to provide (block 112) the view of the hand(s) (or part thereof) of the physician 30 visible through the display 81 while augmenting the display 81 with virtual objects including the three-dimensional view of the interior of the anatomical map 89 of the body part, and the representation 91 of the catheter 40 (and the representations 93 of the electrodes 48) inside the anatomical map 89 responsively to the tracked position of the catheter 40.

In some embodiments, the processor 41 is configured to receive (block 114) user input maneuvering the virtual camera 83 responsively to movement of the head-mounted apparatus 79 or any suitable user interface (such as a joystick). In response to movement of the virtual camera 83, the view of the representation 91 and the anatomical map 89 shown in the display 81 changes.

The processor 41 is configured to recognize (block 116) a gesture of the hand(s) (or part thereof) of the physician 30 selecting a portion of the catheter 40 and/or one of the electrodes 48 of the catheter 40. The processor 41 may recognize the gesture based on: analysis of the images captured by the camera 77; and/or analysis of the images displayed on the display 81; and/or other gesture tracking methods, for example, tracking glove movement. The proximity of the hand or finger(s) to the portion of the catheter 40 or one of the electrodes 48 may be determined from: analysis of the images displayed on the display 81; and/or the tracked position of the catheter 40 and/or the electrodes 48 with respect to a tracked position of the hand(s) or finger(s). The gesture may include any one or more of the following, by way of example: a pinching gesture; a pointing gesture; or a touching gesture.

The processor 41 is configured to perform (block 118) an action responsively to recognizing selection by the physician 30 of the portion of the catheter 40 (or of one of the electrodes 48). Example action now follow. In some embodiments, the processor 41 is configured to render to the display 81 the IEGM 95 responsively to the sensed electrical activity of the selected electrode 48 and recognizing the gesture of selecting that electrode 48. In some embodiments, the processor 41 is configured to generate an electro-anatomical map responsively to the sensed electrical activity of the selected electrode 48 and recognizing the gesture of selecting that electrode 48.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g., "about 90%" may refer to the range of values from 72% to 108%.

Various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination.

The embodiments described above are cited by way of example, and the present invention is not limited by what has been particularly shown and described hereinabove. Rather the scope of the invention includes both combinations and sub-combinations of the various features described hereinabove, as well as variations and modifications thereof which would occur to persons skilled in the art upon reading the foregoing description and which are not disclosed in the prior art.

What is claimed is:

1. A medical system comprising:
   a catheter configured to be inserted into a body part of a living subject;
   a display configured to provide a view of at least part of a hand of a user; and
   a processor configured to:
      track a position of the catheter in the body part;
      render to the display a three-dimensional view of an interior of an anatomical map of the body part and a representation of the catheter inside the anatomical map responsively to the tracked position, while the display is providing the view of the at least part of the hand of the user;
      recognize a gesture of the at least part of the hand of the user selecting a portion of the catheter, the portion of the catheter comprising an electrode configured to sense electrical activity from tissue of the body part; and
      render to the display an intracardiac electrogram in response to (1) the sensed electrical activity and (2) recognizing the gesture as selecting the electrode.

2. The system according to claim 1, further comprising a camera configured to capture an image of the at least part of the hand of the user, wherein the processor is configured to recognize the gesture of the at least part of the hand of the user selecting the portion of the catheter responsively to the tracked position of the catheter and the captured image.

3. The system according to claim 2, further comprising a head-mounted apparatus configured to be worn by the user, and including the display, which is configured to concurrently render to the display: the three-dimensional view of the interior of the anatomical map of the body part; the representation of the catheter inside the anatomical map responsively to the tracked position; and the image of the at least part of the hand of the user captured by the camera.

4. The system according to claim 1, further comprising a head-mounted apparatus configured to be worn by the user, and including the display, which comprises an optical see-through display configured to provide the view of the at least part of the hand of the user visible through the display while augmenting the display with virtual objects including the three-dimensional view of the interior of the anatomical map of the body part, and the representation of the catheter inside the anatomical map responsively to the tracked position.

5. The system according to claim 1, wherein:
the catheter includes a plurality of electrodes;
the processor is configured to track a position of each electrode of the plurality of electrodes; and
the processor is configured to recognize the gesture of the at least part of the hand of the user selecting one electrode of the plurality of electrodes of the catheter.

6. The system according to claim 5, wherein
the processor is further configured to generate an electro-anatomical map responsively to the sensed electrical activity and recognizing the gesture selecting the one electrode.

7. The system according to claim 5, wherein the gesture includes any one or more of the following: a pinching gesture; a pointing gesture; or a touching gesture.

8. The system according to claim 1, further comprising a head-mounted apparatus configured to be worn by the user, and including the display, and wherein the processor is configured to:
receive user input maneuvering a virtual camera responsively to movement of the head-mounted apparatus; and
render to the display the three-dimensional view of the interior of the anatomical map of the body part and the representation of the catheter inside the anatomical map as viewed from the virtual camera, while the display is providing the view of the at least part of the hand of the user.

9. The system according to claim 1, wherein:
the catheter comprises an expandable distal end assembly, and a plurality of electrodes disposed on the expandable distal end assembly; and
the processor is configured to render to the display the three-dimensional view of the interior of the anatomical map of the body part and the representation of the catheter inside the anatomical map as viewed from a virtual camera disposed inside the expandable distal end assembly, while the display is providing the view of the at least part of the hand of the user.

10. A medical method, comprising:
providing a view of at least part of a hand of a user on a display;
tracking a position of a catheter in a body part of a living subject;
rendering to the display a three-dimensional view of an interior of an anatomical map of the body part and a representation of the catheter inside the anatomical map responsively to the tracked position, while the display is providing the view of the at least part of the hand of the user;
recognizing a gesture of the at least part of the hand of the user selecting a portion of the catheter, the portion of the catheter comprising an electrode configured to sense electrical activity from tissue of the body part; and
generating an electro-anatomical map in response to (1) the sensed electrical activity and (2) recognizing the gesture as selecting the electrode.

11. The method according to claim 10, further comprising capturing an image of the at least part of the hand of the user, wherein the recognizing includes recognizing the gesture of the at least part of the hand of the user selecting the portion of the catheter responsively to the tracked position of the catheter and the captured image.

12. The method according to claim 11, wherein:
the display is comprised in a head-mounted apparatus to be worn by the user; and
the rendering includes rendering to the display: the three-dimensional view of the interior of the anatomical map of the body part; the representation of the catheter inside the anatomical map responsively to the tracked position; and the captured image of the at least part of the hand of the user.

13. The method according to claim 10, wherein:
the providing includes providing the view of the at least part of the hand of the user visible through an optical see-through display comprised in a head-mounted apparatus to be worn by the user, while augmenting the display with virtual objects including the three-dimensional view of the interior of the anatomical map of the body part, and the representation of the catheter inside the anatomical map responsively to the tracked position.

14. The method according to claim 10, further comprising tracking a position of a plurality of electrodes of the catheter, and wherein the recognizing includes recognizing the gesture of the at least part of the hand of the user selecting one electrode of the plurality of electrodes of the catheter.

15. The method according to claim 14, further comprising sensing electrical activity from tissue of the body part by the one electrode, and wherein the rendering further includes rendering to the display an intracardiac electrogram responsively to the sensed electrical activity and the recognizing the gesture selecting the one electrode.

16. The method according to claim 14, wherein the gesture includes any one or more of the following: a pinching gesture; a pointing gesture; or a touching gesture.

17. The method according to claim 10, further comprising receiving user input maneuvering a virtual camera responsively to movement of a head-mounted apparatus worn by the user, and wherein the rendering includes rendering to the display the three-dimensional view of the interior of the anatomical map of the body part and the representation of the catheter inside the anatomical map as viewed from the virtual camera, while the display is providing the view of the at least part of the hand of the user.

18. The method according to claim 10, wherein the rendering includes rendering to the display the three-dimensional view of the interior of the anatomical map of the body part and the representation of the catheter inside the anatomical map as viewed from a virtual camera disposed inside an expandable distal end assembly of the catheter, while the display is providing the view of the at least part of the hand of the user.

19. A software product, comprising a non-transient computer-readable medium in which program instructions are stored, which instructions, when read by a central processing unit (CPU), cause the CPU to:

track a position of a catheter in a body part of a living subject;

render to a display a three-dimensional view of an interior of an anatomical map of the body part, and a representation of the catheter inside the anatomical map responsively to the tracked position, while the display is providing a view of at least part of a hand of a user;

recognize a gesture of the at least part of the hand of the user selecting a portion of the catheter, the portion of the catheter comprising an electrode configured to sense electrical activity from tissue of the body part; and render to the display an intracardiac electrogram in response to (1) the sensed electrical activity and (2) recognizing the gesture as selecting the electrode.

* * * * *